(12) United States Patent
Catelli et al.

(10) Patent No.: US 6,596,231 B1
(45) Date of Patent: Jul. 22, 2003

(54) CONTINUOUS PROCESS FOR HYPERACTIVATION OF FLUIDS FOR STERILIZATION

(75) Inventors: Camillo Catelli, Parma (IT); Marco Musatti, Montecchio (IT)

(73) Assignee: Tetra Laval Holdings & Finance S.A., Pully (CH)

( * ) Notice: Subject to any disclaimer, the term of this patent is extended or adjusted under 35 U.S.C. 154(b) by 0 days.

(21) Appl. No.: 09/555,880

(22) PCT Filed: Dec. 10, 1998

(86) PCT No.: PCT/IT98/00357

§ 371 (c)(1),
(2), (4) Date: Jun. 8, 2000

(87) PCT Pub. No.: WO99/30747

PCT Pub. Date: Jun. 24, 1999

(30) Foreign Application Priority Data

Dec. 12, 1997 (IT) ........................................ MO97A0225
Feb. 27, 1998 (DE) ........................................ 198 08 318

(51) Int. Cl.[7] ................................................ A61L 2/00
(52) U.S. Cl. ................................ 422/28; 422/1; 422/33
(58) Field of Search ............................ 422/28, 33, 292, 422/300, 302

(56) References Cited

U.S. PATENT DOCUMENTS 6,132,680 A  * 10/2000 Addy et al. ................... 422/33

* cited by examiner

*Primary Examiner*—Krisanne Thornton
(74) *Attorney, Agent, or Firm*—Browdy and Neimark, P.L.L.C.

(57) ABSTRACT

The continuous process for hyperactivation of fluids for sterilization uses a sterilizing fluid which is mixed with a gas that is inert with respect to the fluid. A sterilizing mixture is obtained which is subsequently evaporated by means of introduction into an evaporation tube in a condition of annular motion, where a liquid phase of the mixture flows against the heated walls of the evaporator at a slower speed than the gaseous phase thereof, which flows in the central zone of the evaporator, internally of the liquid phase. A gaseous vapour/inert gas mixture is thus obtained, which is subjected to a waiting period during which the mixture flows through a transit device which transfers it to a sterilization chamber, a temperature of which is lower than a dewpoint temperature of the gaseous mixture, where a product is sterilized.

23 Claims, 1 Drawing Sheet

CONTINUOUS PROCESS FOR HYPERACTIVATION OF FLUIDS FOR STERILIZATION

CROSS REFERENCE TO RELATED APPLICATION

Figure 1:
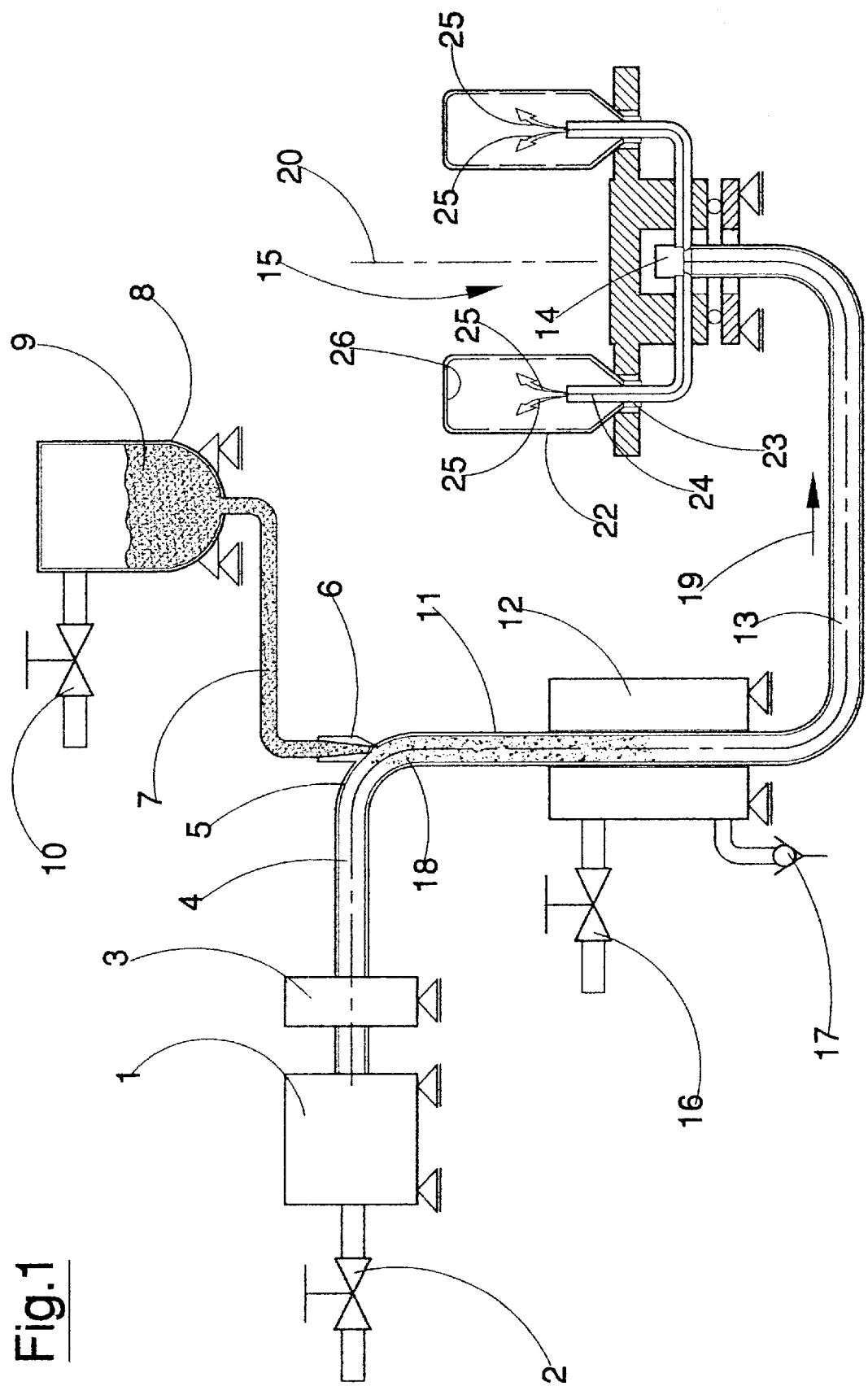

The present application is the national stage under 35 U.S.C. 371 of PCT/IT98/00357, filed Dec. 10, 1998.

1. Technical Field

The invention relates to a continuous process for hyperactivation of fluids for sterilization.

Specifically but not exclusively the invention is usefully applied for the hyperactivation of sterilizing chemical agents of known type, such as hydrogen peroxide, peracetic acid, chlorine dioxide, hypochlorites, chlorates, oxidants based on bromine—iodine—fluorine etc., intended to be subsequently used for sterilizing surfaces of any kind, such as paper, plastics, metal, organic material etc., belonging to various objects intended for the most varied fields of application, such as the food, pharmaceutical, medical, electronic industries.

2. Background Art

The above-mentioned substances have been used for sterilization for some time in that their sterilizing properties are well known. Moreover, the data (concentration, temperature and contact time) relating to their use in this kind of application is generally provided by the manufacturers themselves. Sterilization processes which employ the above-mentioned agents for sterilizing surfaces and containers of paper or multi-layer board for foodstuffs in particular have also been known for some time.

One of these processes teaches spraying a sterilizing solution onto the surface to be treated and then activating it by heating it up and causing evaporation thereof, obtaining active radicals, effective in the sterilization action, in direct contact with the surface to be sterilized.

Another of these processes teaches mixing the sterilizing solution with an inert gas and subsequently heating the mixture to obtain a gaseous vapour/inert gas mixture which is immediately blown onto the material to be sterilized, where the vapour condenses. This second process is described in U.S. Pat. Nos. 4,742,667 and 4,631,173.

Both these processes have the drawback of needing a high operating temperature in order to obtain a large number of active radicals, and cannot therefore be used for materials which degrade at moderate temperatures of the order of 50–70° C. A further problem in the above-cited prior art processes is that the gaseous vapour/inert gas mixture which is obtained, given the high temperature, is very rich in active radicals but is not controllable; there is therefore virtually instantaneous combination among the active radicals, which tends to destroy or render uncertain the sterilizing power of the mixture. For this reason it is essential that the activated mixture is immediately brought into contact with the material to be sterilized. For this purpose, in the first process the gaseous mixture is obtained directly in contact with the material to be sterilized, whereas in the second process the material to be sterilized is in contact with the outlet zone of the evaporator. This clearly leads to serious limitations in terms of plant construction, in that the gaseous mixture has to be used in the same zone in which it is produced. The difficulty of controlling the gaseous mixture, together with the tendency of the active radicals to combine together, also increases the time required for reliable sterilization of the materials.

The main object of the invention is to eliminate the above-mentioned disadvantages by providing a process which enables a sterilizing gaseous mixture to be obtained which is rich in radicals, which are activated and uniformly distributed in the mixture and the chemical/physical state of which can be controlled for relatively long periods of time.

A further object of the invention is to provide a process which enables the gas production zone of the sterilizing gaseous mixture to be separated from the zone the of its use.

A further object of the invention is to provide a process which enables the sterilizing gaseous mixture to be obtained and used at temperatures which are moderate and in any event lower than the boiling point of the sterilizing solution. An advantage of the invention is that it enables the sterilizing gas mixture to be used to sterilize heat-sensitive materials.

A further advantage of the invention is that it reduces the operating costs and consumption of the sterilizing processes and reduces the residues of sterilizing agent on the treated surfaces.

A still further advantage of the invention is that it enables a sterilizing gaseous mixture to be obtained which reduces the sterilizing times of the treated surfaces. These and further advantages and objects are all achieved by the invention as it is characterized in the appended claims. Some substantially similar practical applications of the process are also described, the last of which involves a more detailed description aided by an illustration in the form of a drawing.

Further features and advantages of the invention will emerge more clearly from the detailed description which follows of the various phases of the said process, provided by way of a non-limiting example, and illustrated in the accompanying drawing, in which:

FIG. 1 is a highly schematic diagram of a plant for sterilizing PET bottles having an orifice which is disposed downwards and having a base which is disposed upwards in such a way that the gas mixture can be blown into the bottle interior in an upwards direction.

DISCLOSURE OF INVENTION

The continuous process of the invention comprises a phase of mixing a sterilizing solution, containing a predetermined percentage of active ingredient, with a gas which behaves inertly with respect to the sterilizing solution (pilot gas); this mixing is preferably done by atomizing the sterilizing solution into a stream of the pilot gas, which is moving turbulently. The velocity of the gas stream is between 15 and 50 m/s; the temperature of the pilot gas is usually close to ambient temperature; the pilot gas, generally supplied by a compressor, may be air, nitrogen or another gas which behaves inertly with respect to the sterilizing solution, or which does not react with it.

The ratio between the flow rate of the inert gas, expressed in Nmc/h, and the flow rate of the sterilizing liquid, expressed in 1/h, is between 5 and 50 inclusive. By means of this mixing phase, a two-phase sterilizing mixture is obtained which is introduced into a tubular evaporator, the walls of which are heated to a temperature below the boiling point of the sterilizing solution, as the liquid evaporates without being brought to boiling point, as will be explained more clearly herein below.

As stated, in the evaporator the volumetric ratio between the flow rates of the pilot gas and the sterilizing solution is normally in the range 5–50 inclusive while the velocity of the pilot gas is relatively high (15–50 m/s). In these conditions an annular motion condition of the two-phase mixture is obtained: the liquid phase adheres to the walls of the exchanger, moving at moderate velocity (0.2–0.5 m/s), while the gas phase occupies the center of the flow section, passing through it in turbulent state. The thickness of the liquid film adhering to the walls of the evaporator does not depend exclusively on the liquid flow rate, but also on the gas flow rate and also on the geometry of the exchanger. This means that is possible to obtain a considerable number of square meters of liquid/gas interface capable of generating activated radicals and transferring them into the gaseous stream.

The enrichment of the gaseous stream takes place by turbulent transfer of material, diffusion, saturation of the gas stream and by evaporation. All these phenomena contribute to distancing the activated radicals from the liquid phase, where the probability of collision between two radicals is extremely high, by transferring them into the gaseous stream where the probability of collision is reduced by at least one order of magnitude. In other words, it is possible to prolong the life of the activated complex by reducing the probability, of combination between the active radicals.

It should also be borne in mind that in the two-phase stream in annular flow the coefficient of exchange for the liquid phase is relatively low (800–1000 Kcal/hmq ° C.). This is essential in order to prevent excessively high concentrations of activated complexes close to the walls. Furthermore, the coefficient of exchange for the gas phase is very low (50–100 Kcal/hmq ° C.). This means that the central part of the gas phase remains virtually cold, reducing Brownian motion and hence the probability of the active radicals colliding in the gas phase.

The thickness of the liquid phase, which is of the order of fractions of a millimeter, may be controlled by means of the two-phase stream in annular flow. Clearly, the thinner the liquid film the more efficient the process, even if using high gas/liquid ratios reduces the capacity of the mixture to condense in the sterilization chamber, as will be explained in greater detail herein below.

It will be further noted that it is not necessary for the mixture to reach the boiling point of the sterilizing agent. This is of the utmost importance in that, at this temperature, the rate of decomposition of the mixture would be too high and the system would not be easy to control. Use is therefore made of the tendency of the pilot gas to become saturated with vapors, so as to obtain evaporation conditions at temperatures below boiling point.

It is therefore possible to operate at relatively low wall temperatures (40° C.), even though this involves the use of a larger exchange surface and less activation of the radicals which is, however, compensated for by a larger interface surface. The sterilizing mixture may therefore also be used on heat-sensitive materials. Finally it will be noted that the walls of the evaporator do not in practice come into contact with the active radicals which are very corrosive; this greatly reduces the corrosion phenomena which are encountered in apparatus which use other types of processes.

The process further provides a phase of controlling the temperature of the gaseous mixture which may be carried out either simultaneously with or immediately after the evaporation phase and which enables in particular the dew conditions of the gaseous mixture to be controlled, and also enables the gaseous mixture to be kept active for relatively long periods. This phase is generally carried out by means of a very low-energy heat exchanger, or with minimal temperature difference between the heated fluid and the heating fluid, which is physically separate from the evaporator but which could be physically either separate from or incorporated in the evaporator.

Further to the evaporation phase the process in question provides a waiting time, between 0.5 and 2 seconds inclusive, between the emergence of the gaseous mixture from the evaporator and its introduction into a sterilization chamber in which contact takes place between the gaseous mixture and the material to be sterilized, with consequent sterilization of the material. It will be noted that a waiting time of between 0.5 and 2 seconds inclusive is very long in relation to to the kinetics of the molecular mechanisms involved.

During this waiting time the gaseous mixture flows through a transit device, generally constituted by a tubular element which connects the evaporator to the sterilization chamber and which emerges into the sterilization chamber through a choke, such as a distribution nozzle, which accelerates the mixture entering the sterilization chamber. Temperature and degree of saturation of the mixture are kept at pre-set values in this transit device. This permits control over the physico-chemical properties of the gaseous mixture, making the process very reliable and repeatable.

The temperature inside the sterilization chamber is lower than the dewpoint of the gaseous mixture; in this way an active mist is created inside the chamber, which surrounds the material to be sterilized and sterilizes it. A cooling phase of the sterilization chamber may be provided in order to obtain this feature.

Given that the use of activated complexes and/or radicals in gaseous phase does not guarantee an efficient sterilizing effect, in that only a fraction of them may lap the surface to be sterilized, the gaseous mixture should be capable of condensing on the surface of the material to be sterilized and not elsewhere, since during condensation there is a re-concentration of the radicals in liquid phase, followed by a rapid degradation of the activated complexes.

To obtain this behavior the pilot gas must be saturated with the sterilizing solution and this state maintained throughout the entire waiting time; in fact, if the gaseous mixture were to begin to condense during the waiting time, or in the transit device, there would be a gradual flooding of the distribution nozzle and above all a rapid decline in the bactericidal power. Reaching saturation is not absolutely necessary; it is sufficient for the gaseous mixture, cooling by expansion from the distribution nozzle, to reach a temperature below the dewpoint.

If the waiting time and the velocity of the mixture are considered it will be seen at once that the tubular element which constitutes the transit device may be very long (of the order of tens of meters); this fact is very interesting when considering plant construction, as the zone in which the sterilizing gaseous mixture is produced can be separated from the zone in which it is used. This, together with the other features, means that the process can be used in any type of installation comprising a zone for sterilization by chemical means. It should be pointed out, however, that the waiting time may also be dispensed with and the gaseous mixture be used immediately after its emergence from the evaporator if required. This could lead to an albeit slightly greater efficiency of the gaseous mixture at the expense, however, of the flexibility of the process and less control over its reliability and repeatability.

The process in question has been described in terms of its fundamental characteristic aspects insofar as many of the values of the magnitudes involved are neither all-important nor critical as regards correct use of the process. In fact a basic advantage of the process lies in the fact that many process parameters may be varied as operational needs dictate, whilst effective control of the gaseous mixture and its sterilizing efficacy are consistently maintained. The following will therefore provide both elements of a general nature for determining values for the magnitudes in question and an embodiment of the process with the associated results obtained, by way of example.

The following values are generally known, or selected by the designer:

the type of sterilizing solution, which the designer may freely select from those of known type and properties;

the type of pilot gas, which is generally sterile air but may be freely chosen by the designer;

the flow (QL) of the sterilizing solution;

the concentration (X) of the sterilizing agent (generally defined on the basis of problems of corrosion or of limiting product residue on the surface to be sterilized);

the decomposition temperature (TD) of the sterilizing agent (temperature at which the compound decomposes and loses all its bactericidal action);

the maximum temperature (TP) the surface of the material to be sterilized can withstand;

the temperature (TS) of the sterilizing gaseous mixture, which is not critical but which the designer may define within fairly wide values provided that they are lower than TD.

The compressor, or other technically equivalent device for supplying the pilot gas stream, is so dimensioned as to provide a gas flow rate of 5 to 50 times QL with a head equal to the total load losses of the circuit which are largely concentrated in the distribution nozzle; the nozzle must operate at a particularly high velocity (60–120 m/s) to produce, in addition to expansion, rapid diffusion of the gaseous mixture into the sterilization chamber.

With the pressure downstream of the compressor and the flow rates of sterilizing solution and pilot gas being known, the dewpoint of the mixture can be calculated. The evaporator and/or very low-energy heat exchanger (thermostat) outlet temperature should be at least 10° C. higher than the dewpoint so as to prevent condensation of the mixture in the transit device.

Finally the temperature of the sterilization chamber is defined; it should be at least 10° C. lower than the dewpoint of the mixture.

When the sterilizing mixture (at temperature TS) expands from the distribution nozzle its high velocity ensures rapid cooling, chiefly due to mixing with the air present in the sterilization chamber. By means of a correct dimensioning of the distribution nozzle the constraint relating to the temperature TP can be respected independently of the value of the temperature TS.

As will easily be seen, there are no particularly critical factors in the process of the invention; the basic aspect, in practice, is successful obtaining of an annular flow of the two-phase fluid.

First Practical Example sterilizing solution: 4.5% Oxonia Aktiv P3 (Henkel—active ingredient 5% peracetic acid) in demineralized water;
pilot gas: sterile air;
QL: 55 l/h;
TD: 100° C.;
TP: 63° C. (PET bottles);
TS: 70° C.;
Velocity in the evaporator: 20 m/s
Pressure at the evaporator: 0.4 bars
Waiting time: 1 second
Velocity at the distribution nozzle: 90 m/s
Temperature of the sterilization chamber: 15° C.

By adopting this process to sterilize PET bottles, a time of just 3 seconds for a decimal reduction of spores of B. Subtilis was obtained, which is a much shorter time than both the time quoted by the manufacturer of the solution for its use as aqueous solution and than the time which was determined experimentally using a process of previously known type with a solution of the same concentration (4.5%) and brought to the same temperature (70° C.); a time of approx. 30 seconds for a decimal reduction of spores of B. Subtilis was obtained in this latter test.

Other Practical Examples

The object of sterilization is achieved by the invention if the sterilizing agent is atomized into an air stream and the mist is heated by heat supply to a temperature of between 25° C. and 80° C. and is blown by means of the air carrier in the gas phase onto the surface which is to be sterilized and is at about 10° C. to 30° C., so that condensable components of the gas condense on the surfaces. The sterilizing agent, which contains peracetic acid in a concentration of 0.1% to 1.5%, is liquid and is preferably sprayed into an air stream with the aid of a high-pressure nozzle so that the liquid sterilizing agent is dispersed to give a mist, which is why the term "atomization" is used here. The air stream now carries the mist, i.e. the liquid sterilizing agent finely divided into droplets, so that a mixture of air and sterilizing agent is transported. The mist present in this stream is heated to between 25° C. and 80° C. by heat supply, preferably in a heat exchanger, so that the mist vaporizes. The total stream, i.e. the mixture described, is now in the gas phase. The stream of the mist with the air carrier is then blown onto that surface of the package which is to be sterilized. The temperature of the flowing gas mixture is chosen so that the condensable components of the gas blown onto the package condense since these surfaces to be sterilized are at a temperature of only 10° C. to 30° C.

A surprising advantage is that a very wide range of packages, for example hollow bodies and their covers, can be sterilized in a time substantially shorter than 2 minutes, and this can be done in spite of the low temperature of the surfaces to be sterilized, which is in the range between 10° C. and 30° C. This makes it possible to save considerable quantities of energy, to save space, use smaller machine units and consume fewer chemicals.

It is particularly preferable if, according to the invention, the peracetic acid is present in the sterilizing agent in a concentration of 0.2% to 0.3%. Owing to the low concentration of the chemicals contained in the sterilizing agent, any existing migration into plastic surfaces is considerably slowed down so that there is no fear of falsification of food by residues in the case of packages sterilized by the process according to the invention. Nevertheless, 99.99% of bacterial spores are killed at the relatively low temperatures mentioned here.

In a further embodiment of the invention it is envisaged that the sterilizing agent is fed to the air stream in an amount of 10–100 liters per hour, preferably an amount of 55 liters per hour. Thus, at the low concentration of the sterilizing agent used, only small amounts of chemicals are employed over the short time of exposure, and nevertheless a 99.99% kill is achieved. The above-mentioned amount of sterilizing agent makes it possible to achieve more or less saturation of the air stream at the stated temperatures, for example in the range from 25° C. to 80° C., with the result that, when the gas mixture strikes the surfaces to be sterilized, condensation also takes place on said surfaces and leads to wetting of the surfaces with the liquid sterilizing agent and thus ensures killing.

It is furthermore advantageous according to the invention if P3-oxonia active is used in a concentration of 3% to 10%, preferably of 6%, as the sterilizing agent. The dilution is achieved by mixing demineralized water with the commercial product oxonia active. Owing to the low concentration, smaller amounts of the sterilizing agent than would have been expected are required. This gives rise to the further advantage that the accompanying phenomena of the sterilization process are more advantageous because, for example, a smaller amount of foul-smelling compositions need be used. Owing to the low concentration of the oxonia active, less time and/or not such large quantities of heat or air are required for dying than would be expected in the case on known processes. The fact that the sterilizing agent need not at all be specially dried in the process according to the invention may be regarded as a further advantage. All that is envisaged is washing to remove the chemicals.

The process can be carried out particularly advantageously when, according to the invention, the air flows continuously. Air is used as a carrier for applying the sterilizing agent to the surface to be sterilized. After passing through a sterile filter, said air can be brought into a continuous flow in a simple and economical manner, and the liquid sterilizing agent is then added to said flow when the process starts.

It is particularly expedient if, according to the invention, the air stream has a throughput of 100 to 600 cubic meters per hour, preferably a throughput of about 360 cubic meters per hour.

If the above-mentioned amounts of sterilizing agent, for example 10 to 100 liters per hour, are introduced into an air stream of this magnitude, a carrier gas saturated with the liquid sterilizing agent is achieved at the surface to be sterilized. This saturation causes immediate condensation of the condensable components of the gas mixture when the latter strikes the relatively cold surfaces of the packaging part.

These conditions can also be obtained and can also be particularly advantageously established if, according to a further measure of the invention, the temperature of the air stream, initially at room temperature and carrying the mist, is in the range between 50° C. and 70° C. after it has been heated. The energy-saving loading of a plant for carrying out the sterilization process according to the invention is recognized when it is noted that the air stream is initially at room temperature. The mists which it carries are caused to vaporize in the stated temperature range so that the gas phase is then present in the gas mixture, i.e. in the flow. On the other hand, in an advantageous use of the process according to the invention, the package to be sterilized can be heated by only, for example, 2° C. from its original temperature, for example room temperature.

In a further advantageous embodiment of the invention, the air stream carrying the mist is blown within a period of 5 seconds to 20 seconds, preferably about 10 seconds, on to the surface to be sterilized. This air stream, which is the gas mixture described above, in which the liquid sterilizing agent is present after vaporization of the mist, thus acts not for 2 to 3 minutes, but only for up to 20 seconds on that surface of the package which is to be sterilized. Owing to this short cycle time in combination with the low concentration of the sterilizing agent and also the low temperature of use, there are advantageously only very small residual amounts of sterilizing agent in the contents at the end. The values measured here and obtained from experiments were well below the prescribed limits of the relevant regulations.

If it is intended precisely to measure the beginning and the end of the measured period of action of the sterilizing agent in exact experiments, it is necessary to begin with the flow of h gas mixture on to the surface to be sterilized and to end at the moment when the supply of the gas just blown onto the surface to be sterilized is interrupted.

It is preferable if, according to the invention, the package is a hollow body into whose interior the air stream carrying mist is blown against gravitational force. The stream containing the gas mixture comprising air/vaporized sterilizing agent is blown upwards through the orifice of a hollow body, with a vertical component. The sterilizing agent constitutes the condensable components, condenses immediately after striking the inner surface of the hollow body and forms a liquid film wetting this surface to be sterilized. This liquid wets the surface, and the overflow drips out downwards from the introduction orifice in the direction of the gravitational force. In the 5 to 20 seconds exposure time or residence time of the packaging part in the sterilization space, there is no accumulation of a relatively large amount of liquid, so that a short washing time with demineralized water is sufficient for removing any chemicals.

The condensation, wetting and consequently sterilization also take place in the neck region of a hollows packaging element (a bottle or the like). Sterilization effects are even found on the outside and the back (outside of base) of the hollow body with a certain intensity, even if with a reduced intensity.

According to a further consideration of the invention, the sterilization chamber in a machine for carrying out the process according to the invention can be exposed to cold sterile air, for example sterile air at room temperature preferably 10° C. The result is then cooling of the package to be sterilized and hence good condensation at the dew point. Passing in cold sterile air results in independence of the ambient temperature. Even if the packaging to be sterilized initially has temperatures of up to 30° C. in the summer or in a hot country, its temperature decreases as a result of this stated exposure to cold sterile air. The condensation effect can be considerably enhanced by this small additional outlay.

The known processes disclosed at the ouset and using the liquid oxonia active on the one hand and using the highly concentrated hydrogen peroxide on the other hand can be more simply designed taking into account the teaching according to the invention, explained above.

Only, a fraction of the amount of sterilizing agent is required in comparison with the large amounts in the known processes in which packaging parts, for example platic bottles (PET) were completel filled with the liquid sterilizing agent. In this experiment, an air stream at a temperature of 45° C. to 150° C. (preferably 50° C. to 70° C.) was used as a carrier for oxonia active. The oxonia solution is atomized into the air stream by means of a nozzle. The liquid/air mixture is then heated to a temperature at which the air is virtually saturated. The air containing the oxonia active is transported to the packaging to be sterilized, the sterilization chamber in the filling machine considered in this experiment being kept at a temperature below the dew point. Here use was made of the concept of supplying the sterilization chamber with cold sterile air in order always to obtain good condensation at the dew point. The package with a temperature below the dew point (preferably ambient temperature) was introduced into the sterilization. chamber, the orifice of the packaging being arranged at the bottom. The air containing the liquid oxonia was blown into the hollow body of the package via thin blow-in tubes. The oxonia active condensed on the cold packaging surfaces, both on the inside and on the outside. This took place in a treatment time, the treatment being comparable with that in the case of film condensation. The oxonia concentration in the condensation film is about the same as in the case of the solution which was used for atomization into the air. When the first of these experiments was carried out, contact times of a few minutes for achieving the required killing of the bacterial spores were expected.

Surprisingly however the spores were killed, i.e. the packaging was sterilized, in only a few seconds.

Furthermore, the low concentration of the sterilizing agent results in the advantage of no corrosion on the endangered parts of the sterilization and filing a machine. Apart from the above-mentioned lower energy consumption, it has also proved advantageous that the low temperatures used for the surface to be sterilized, i.e. temperatures of the package less than 65° C., makes it possible surprisingly readily to sterilize PET bottles, too, by the novel process according to the invention. The other secondary effect of the low temperatures is the low absorptivity of the surface of a PET bottle with respect to absorption of peroxide and peracetic acid by migration. Covers and any type of closure parts for packaging in the form of hollow bodies can also very readily be sterilized by the process according to the invention. The critical surfaces of a closure are preferably directly exposed to the gas mixture, and those surfaces of such parts and closures which are adjacent or behind nevertheless come into contact with sterilizing agent and hence undergo sterilization in a short time and at a low temperature.

In a further embodiment of the invention, made with reference to the figure of the drawing, air at room temperature is brought to a pressure of about 0.4 bar in a compressor 1 and, after passing through a sterile air filter 3 (to become in effect the inert pilot gas of the invention) is forced into the main pipe 4. This has an elbow 5 on the outside of which an atomising nozzle 6 is mounted.

The nozzle 6 is connected to a fixed pressure tank 8 via a supply pipe 7. The tank 8 contains a sterilizing liquid 9 under a pressure of 3 bar. Fresh sterilizing liquid 9 can optionally be introduced into the tank 8 via the valve 10.

The main pipe 4 for carrying the air stream develops vertically, downstream of the upper elbow 5, becoming a tubular evaporator 11 for the sterilizing liquid/pilot gas mixture. The evaporator 11 passes through a heat exchanger 12 and is conducted through a further extension of the evaporator 11, denoted gas pipe 13, to the distribution space of a filling machine, denoted in its entirety by 15.

The heat exchanger 12 is arranged along the development of the evaporator 11 and in the present embodiment is heated by steam via the valve 16. The heating medium is expelled via the condensate trap 17.

Below the nozzle 6 the liquid droplets atomized into the invisible air steam are indicated in the form of mist 18. The droplets are shown to be smaller and in a smaller number in the region of the heat exchanger 12 in the downward direction of flow of the air. Thus a virtually pure gas mixture is transported in the gas pipe 13 in the direction of the arrow 19.

A turntable 21, which is represented schematically and which exhibits only two stations, each bearing a package 22 containing the surfaces to be sterilized, rotates about the axis 20 of a filling machine 15 which doubles as a sterilization chamber, which axis is indicated by a dash-dot line. The package 22 is a PET bottle, the orifice 23 of which is inserted downwards through the orifice in the turntable 21. The feed tube 24 is led from below through the bottle orifice 23 into the interior of the PET bottle and terminates therein, at about a third of the bottle length. The arrows 25 indicate the gas mixture emerging from the feed tube 24 into the interior of the PET bottle. The dashed line 26 along the inner surface of the PET bottle represents the liquid film of the sterilizing liquid condensed from the gas phase. The film can drip downwards (not illustrated), past the outside of the feed tube 24 through the orifice 23 and can be collected there by means for collecting (not illustrated).

In the system and, embodiment illustrated, a 6% solution of P3-oxonia activa is kept under 3 bar in the pressure tank 8 and sprayed through the nozzle 6 into the air stream having a throughput of 360 cubic meters per hour, at a rate of 55 liters per hour. This results in the mist of gas/sterilizing liquid in the evaporator 11. As a result of the vaporization in the evaporator 11, which is heated by the heat exchanger 12, the temperature of the gas/sterilizing liquid mixture in the gas pipe 13 is 70° C.

This gas/sterilizing liquid mixture is directed, as indicated by the arrows 25, via the feed tubes 24 on to the inner surface of the PET bottle which is approximately at room temperature, condenses there and forms the condensate film 26. These condensable constituents of the gas are predominantly water, peroxide and peracetic acid. In an experiment, about 25 liters of gas were allowed to flow into each PET bottle for 10 seconds. A resultant 99.99% of bacterial spores were killed, an outstanding outcome.

What is claimed is:

1. In a continuous process for hyper-activation of fluids for sterilization, comprising the phases of:

mixing the sterilizing solution with a gas which is inert with respect to the sterilizing solution, so as to obtain a two-phase inert gas/sterilizing solution sterilizing mixture;

evaporating the sterilizing solution contained in a mixture to form a gaseous vapour/inert gas mixture;

blowing the gaseous mixture onto the material to be sterilized where the vapour condenses;

the improvement wherein the evaporation phase is carried out by introducing the two-phase sterilizing mixture into a tubular evaporator with a flow of annular motion in which the liquid phase of the mixture passes over heat exchange walls of the evaporator at a reduced velocity compared with the velocity of the gaseous phase of the mixture which passes through the central zone of the evaporator.

2. The process of claim 1, wherein:

the phase of mixing the sterilizing solution with an inert gas is carried out by atomizimg the sterilizing solution into a stream of inert gas;

the sterilizing mixture obtained is introduced into the tubular evaporator.

3. The process of claim 2, wherein said stream of inert gas has a velocity of between 15 and 50 m/s inclusive.

4. The process of claim 2, wherein the ratio between the flow rate of inert gas, expressed in Nmc/h, and the flow rate of the sterilizing liquid, expressed in l/h, is between 5:1 and 50:1 inclusive.

5. The process of claim 1, wherein the wall temperature of the evaporator is lower than the boiling point of the sterilizing solution.

6. The process according to claim 1, wherein:

a waiting time is provided, between 0.5 and 2 seconds inclusive, between an emergence of the gaseous mixture from the evaporator and introduction thereof into a sterilization chamber, in which sterilization chamber the contact between the gaseous mixture and the material to be sterilized takes place;

during the waiting time the gaseous mixture passes through a transit device which connects the evaporator to the sterilization chamber and which emerges into the sterilization chamber through a choke, in which temperature and degree of saturation of the mixture are maintained at pre-determined values.

7. The process of claim 6, wherein the temperature inside the sterilization chamber is lower than a dewpoint of the gaseous mixture.

8. The process of claim 1, comprising a phase of controlling the temperature of the gaseous mixture, which phase is carried out simultaneously with or immediately after the evaporation phase.

9. The process of claim 2, wherein said stream of inert gas moves with turbulent motion.

10. The process of claim 7, comprising a phase of cooling the sterilization chamber.

11. A process for sterilizing packages (22) with a sterilizing liquid (9) containing peracetic acid in a concentration of from 0.1% to 1.5%, which sterilizing liquid (9) wets surfaces of the packages (22) to be sterilized, kills bacterial spores thereon and is then removed, wherein the sterilizing liquid is atomized into a stream of sterile air and a resulting mist (18) is heated by a heat exchanger (12) to a temperature of between 25° C. and 80° C. before being blown, with the sterile air/sterilizing liquid mixture in a gas phase on to the surfaces of the packages (22) to be sterilized, which surfaces are at a temperature of between 10° C. to 30° C. and which cause condensable constituents of the sterile air/sterilizing liquid mixture to condense thereon.

12. The process of claim 11, wherein the peracetic acid is present in the sterilizing liquid (9) at a concentration of between 0.2% and 0.3%.

13. The process of claim 11, wherein the sterilizing liquid (9) is fed into the stream of sterile air in an amount of from 10 to 100 liters per hour.

14. The process of claim 11, wherein the sterilizing liquid. (9) contains P3-oxonia active in a concentration of from 3% to 10%.

15. The process of claim 11, wherein the sterile air is made to flow continuously.

16. The process of claims 11, where the flow of sterile air has a throughput of from 100 to 600 cubic meters per hour.

17. The process of claim 11, wherein the temperature of the stream of air, initially at room temperature and carrying the sterilizing liquid in the form of vapour, is at a temperature between 50° C. and 70° C. after undergoing a heating process.

18. The process of claim 11, wherein the sterile air/ sterilizing liquid mixture in the gas phase is blown for a period of between 5 to 20 seconds, on to the surfaces to be sterilized.

19. The process of claim 11, wherein the packages (22) are constituted by hollow bodies, internally of which the sterile air/sterilizing liquid mixture is blown in an upwards direction.

20. The process of claim 12, wherein the sterilizing liquid (9) is fed into the stream of sterile air in an amount of about 55 liters per hour.

21. The process of claims 14, where the flow of sterile air has a throughput of from 350 to 450 cubic meters per hour.

22. The process of claims 15, where the flow of sterile air has a throughput of about 360 cubic meters per hour.

23. The process of claim 11, wherein the sterile air/ sterilizing liquid mixture in the gas phase is blown for a period of about 10 seconds, on to the surfaces to be sterilized.

* * * * *